(12) United States Patent
Hagen et al.

(10) Patent No.: US 7,395,119 B2
(45) Date of Patent: Jul. 1, 2008

(54) IMPLANTABLE ELECTRODE ASSEMBLY HAVING REVERSE ELECTRODE CONFIGURATION

(75) Inventors: Jeffrey J. Hagen, Plymouth, MN (US); Mary L. Cole, St. Paul, MN (US); Martin A. Rossing, Coon Rapids, MN (US)

(73) Assignee: CVRx, Inc., Minneapolis, MN (US)

( * ) Notice: Subject to any disclaimer, the term of this patent is extended or adjusted under 35 U.S.C. 154(b) by 178 days.

(21) Appl. No.: 11/133,741

(22) Filed: May 19, 2005

(65) Prior Publication Data

US 2006/0265038 A1    Nov. 23, 2006

(51) Int. Cl.
*A61N 1/00* (2006.01)
(52) U.S. Cl. ...................... 607/116; 607/115
(58) Field of Classification Search ................ 607/116, 607/118, 119, 130
See application file for complete search history.

(56) References Cited

U.S. PATENT DOCUMENTS

| | | | |
|---|---|---|---|
| 3,405,175 A | 10/1968 | Carvallio et al. | |
| 3,421,511 A | 1/1969 | Schwartz et al. | |
| 3,522,811 A | 8/1970 | Schwartz et al. | |
| 3,650,277 A | 3/1972 | Sjostrand et al. | |
| 3,654,933 A | 4/1972 | Hagfors | |
| 3,774,618 A | 11/1973 | Avery | |
| 3,788,329 A * | 1/1974 | Friedman | 607/122 |
| 3,943,936 A | 3/1976 | Rasor et al. | |
| 4,026,300 A | 5/1977 | DeLuca et al. | |
| 4,323,073 A | 4/1982 | Ferris | |
| 4,590,946 A | 5/1986 | Loeb | |
| 4,602,624 A | 7/1986 | Naples et al. | |
| 4,640,286 A | 2/1987 | Thomson | |
| 4,719,921 A | 1/1988 | Chirife | |
| 4,803,988 A | 2/1989 | Thomson | |
| 4,837,049 A | 6/1989 | Byers et al. | |
| 4,940,065 A | 7/1990 | Tanagho et al. | |
| 4,969,468 A | 11/1990 | Byers et al. | |
| 4,979,511 A | 12/1990 | Terry, Jr. | |
| 5,038,781 A | 8/1991 | Lynch | |
| 5,040,533 A | 8/1991 | Fearnot | |
| 5,095,905 A | 3/1992 | Klepinski | |
| 5,174,276 A | 12/1992 | Crockard | |
| 5,199,428 A | 4/1993 | Obel et al. | |
| 5,215,089 A | 6/1993 | Baker, Jr. | |
| 5,251,611 A | 10/1993 | Zehel et al. | |
| 5,265,623 A | 11/1993 | Kroll et al. | |
| 5,282,468 A | 2/1994 | Klepinski | |
| 5,330,515 A | 7/1994 | Rutecki et al. | |
| 5,337,733 A | 8/1994 | Bauerfeind | |
| 5,344,438 A | 9/1994 | Testerman et al. | |

(Continued)

FOREIGN PATENT DOCUMENTS

WO    WO 01/00273 A    1/2001

*Primary Examiner*—Carl H. Layno
*Assistant Examiner*—Brian T Gedeon
(74) *Attorney, Agent, or Firm*—Townsend and Townsend and Crew LLP (57) ABSTRACT

Methods and apparatus for generating an electric field inside a patient include at least a first electrode and a second electrode on a common implantable substrate. Each of the electrodes has a respective proximal end and a respective distal end. Electrical energy can be applied that causes electrical current to flow simultaneously through the first and second electrodes preferentially from the proximal end of one electrode to the distal end of the other electrode.

13 Claims, 12 Drawing Sheets

U.S. PATENT DOCUMENTS

| | | | |
|---|---|---|---|
| 5,351,394 A | 10/1994 | Weinberg | |
| 5,387,234 A | 2/1995 | Hirschberg | |
| 5,411,540 A | 5/1995 | Edell et al. | |
| 5,454,839 A | 10/1995 | Anderson et al. | |
| 5,484,445 A | 1/1996 | Knuth | |
| 5,505,201 A | 4/1996 | Grill, Jr. et al. | |
| 5,540,734 A | 7/1996 | Zabara | |
| 5,540,735 A | 7/1996 | Wingrove | |
| 5,545,202 A | 8/1996 | Dahl et al. | |
| 5,571,150 A | 11/1996 | Wernicke et al. | |
| 5,634,462 A | 6/1997 | Tyler et al. | |
| 5,643,330 A | 7/1997 | Holsheimer et al. | |
| 5,689,877 A * | 11/1997 | Grill et al. | 29/825 |
| 5,700,282 A | 12/1997 | Zabara | |
| 5,707,400 A | 1/1998 | Terry, Jr. et al. | |
| 5,727,558 A | 3/1998 | Hakki et al. | |
| 5,766,236 A | 6/1998 | Detty et al. | |
| 5,779,624 A | 7/1998 | Chang | |
| 5,800,464 A | 9/1998 | Kieval | |
| 5,824,027 A | 10/1998 | Hoffer et al. | |
| 5,861,015 A | 1/1999 | Benja-athon | |
| 5,899,933 A | 5/1999 | Bhadra et al. | |
| 5,919,220 A | 7/1999 | Stieglitz et al. | |
| 5,938,596 A | 8/1999 | Woloszko et al. | |
| 5,989,230 A | 11/1999 | Frassica | |
| 6,006,134 A | 12/1999 | Hill et al. | |
| 6,016,449 A | 1/2000 | Fishell et al. | |
| 6,050,952 A | 4/2000 | Hakki et al. | |
| 6,073,048 A | 6/2000 | Kieval et al. | |
| 6,178,349 B1 | 1/2001 | Kieval | |
| 6,179,776 B1 | 1/2001 | Adams et al. | |
| 6,208,894 B1 | 3/2001 | Schulman et al. | |
| 6,292,703 B1 * | 9/2001 | Meier et al. | 607/118 |
| 6,308,105 B1 | 10/2001 | Duysens et al. | |
| 6,366,815 B1 | 4/2002 | Haugland et al. | |
| 6,438,428 B1 | 8/2002 | Axelgaard et al. | |
| 6,456,866 B1 | 9/2002 | Tyler et al. | |
| 6,522,926 B1 | 2/2003 | Kieval et al. | |
| 6,564,101 B1 | 5/2003 | Zikria | |
| 6,701,189 B2 | 3/2004 | Fang et al. | |
| 6,754,539 B1 | 6/2004 | Erickson et al. | |
| 6,779,257 B2 | 8/2004 | Kiepen et al. | |
| 7,006,875 B1 * | 2/2006 | Kuzma et al. | 607/118 |
| 2002/0005982 A1 | 1/2002 | Borlinghaus | |
| 2002/0103516 A1 | 8/2002 | Patwardhan et al. | |
| 2002/0120178 A1 | 8/2002 | Tartaglia et al. | |
| 2002/0151051 A1 | 10/2002 | Li | |
| 2002/0161281 A1 | 10/2002 | Jaffe et al. | |
| 2003/0040785 A1 | 2/2003 | Maschino et al. | |
| 2003/0050677 A1 | 3/2003 | Gross et al. | |
| 2003/0139781 A1 | 7/2003 | Bradley et al. | |
| 2004/0010303 A1 | 1/2004 | Bolea et al. | |
| 2004/0236387 A1 | 11/2004 | Fang et al. | |
| 2007/0276442 A1 * | 11/2007 | Hagen et al. | 607/2 |

* cited by examiner

IMPLANTABLE ELECTRODE ASSEMBLY HAVING REVERSE ELECTRODE CONFIGURATION

BACKGROUND OF THE INVENTION

Field of the Invention

The invention relates generally to medical devices and methods, and more particularly, to implantable electrodes for applying electrotherapy/electrostimulation that utilizes at least a pair of electrodes employing a reverse electrode configuration.

Implantable electrode assemblies for electrotherapy or electrostimulation are well-known in the art. For example, various configurations of implantable electrodes are described in U.S. Patent Publication No. U.S. 2004/0010303, which is incorporated herein by reference in its entirety. One type of electrode assembly described therein is a surface-type stimulation electrode that generally includes a set of generally parallel elongate electrodes secured to, or formed on, a common substrate or base. Prior to implantation in a patient, the electrodes are generally electrically isolated from one another. Once the electrode assembly is implanted, one or more of the electrodes are utilized as a cathode(s), while one or more of the remaining electrodes are utilized as an anode(s). The implanted cathode(s) and anode(s) are electrically coupled via the target region of tissue to be treated or stimulated.

One example of an application for this type of electrode assembly is for implantation onto a surface of tissue to be the target for electrotherapy or electrostimulation. The target tissue may have an irregular or complex shape, such as the outer surface of a blood vessel. The base or substrate and the electrodes of the electrode assembly can be sufficiently flexible to conform to the shape of the target tissue while maintaining a particular relative positioning of the electrodes. The geometry of the electrode assembly can be especially adapted for implantation at a particular site. For example, an electrode assembly can be sized and shaped to be implanted around the outside of the vascular wall such that the electrotherapy or electrostimulation can be focused on a particular target region.

One known problem associated with state of the art implantable electrode arrangements of certain geometries is their tendency to produce non-uniform electric fields or currents in the target region under certain conditions. An example of such a condition is when the implantation site has a low enough impedance to approach that of the electrode materials. In such cases, the internal resistance of the implanted electrodes becomes a significant parameter in the electrical/electromagnetic model of the implanted electrode arrangements. This problem can become pronounced in electrode arrangements in which the size of the electrodes approaches or exceeds the general size of the target region, or in arrangements in which the electrodes have structural geometries other than merely point electrodes.

Non-uniformity of electric field in the target region can result in sub-optimal electrotherapy or electrostimulation. Another consequence that occurs when the surface regions of implanted electrodes operate with disparate charge densities is an increased susceptibility of the electrodes to corrosion. Because corrosion is a charge density based phenomenon, increased concentrations of charge carriers in certain regions of the electrodes tends to focus faradaic processes responsible for corrosion at those regions.

In U.S. Pat. No. 5,265,623, a defibrillation catheter is described having generally linear electrode geometries (elongate helical or spiral coils) that, when implanted, are both situated generally longitudinally in the heart. The electrodes of the defibrillation catheter are connected to the defibrillation energy source from a center point of each electrode, rather than at the ends thereof. This arrangement is intended to provide an improved field distribution around the catheter electrode and avoid high current densities at the electrode ends. The arrangement nevertheless operates with a charge density gradient in each electrode due to the construction and relative positioning of the electrodes. Thus, the applied electric signaling is not likely to be uniform along the length of the electrodes. Furthermore, the multi-layer or multi-axial construction of the disclosed catheter requires a complex and relatively expensive fabrication process. Moreover, the catheter electrode assembly is not suitable for the surface-type of implantation applications described above.

While techniques have been developed to improve the distribution of electric field densities with respect to axial defibrillation electrode leads, it would be desirable to provide designs for implantable electrodes that improve the distribution of electrical field densities with respect to surface-type implantable electrodes.

BRIEF SUMMARY OF THE INVENTION

The present invention provides methods and apparatus for generating an electric field inside a patient that enhances the effective distribution of the density of the electric field. In one embodiment, at least a first and a second electrode are arranged on a common implantable substrate such that a proximal end of the first electrode is closer to a distal end of the second electrode and vice-versa. The electrodes are arranged and electrically connected to an energy source via the proximal ends such that when electrical energy is applied across the first and second electrodes, electrical current preferentially flows simultaneously through the first and second electrodes from the proximal end of one electrode to the distal end of the other electrode. In one aspect of the invention, the first and second electrodes are situated proximate a surface of tissue to be stimulated such that the electrodes are generally uniformly electrically coupled along their lengths via the tissue.

A method of evenly distributing an electric field between at least a pair of implanted electrodes according to another aspect of the invention includes providing an implantable electrode assembly that includes at least two electrodes on a common substrate, wherein each electrode has an elongate shape and is situated generally equidistantly along its length from at least one of the other electrodes in a configuration where the proximal and distal ends of the electrodes are reversed between an anode and a cathode. Electrical energy is applied through the at least two electrodes such that a generally uniform current density is established between the anode and the cathode.

An electrode assembly according to another aspect of the invention includes a generally flexible base and at least three generally parallel elongate electrode structures secured over a surface of the base, each electrode structure having a proximal end and a distal end. An outer pair of the electrode structures is electrically isolated from an inner electrode structure, and the proximal end of each electrode structure is electrically coupled to a conductive lead adapted to carry electrical energy. The proximal ends of the outer electrode structures and the distal end of the inner electrode structure are proximately situated at a first surface region of the base, and the distal ends of the outer electrode structures and the proximal end of the inner electrode structure are proximately situated at a second surface region of the base that is separate from the first surface region.

Another aspect of the invention is directed to an electrode assembly implanted at an electrotherapy site in a patient, the electrode assembly comprising a substrate; at least two elongate electrodes secured to the substrate and electrically coupled to the electrotherapy site, each electrode having opposing ends proximally and distally situated; and an electrotherapy signal generator circuit electrically coupled with the at least two electrodes and supplying electrotherapy signaling to the electrotherapy site via the at least two electrodes. The electrical coupling facilitates a generally uniform charge density in the at least two electrodes.

An electrotherapy arrangement implanted at an electrotherapy site according to another aspect of the invention comprises an electrode assembly that includes a substrate; and at least two elongate electrodes secured to the substrate and electrically coupled to the electrotherapy site, wherein each electrode is situated such that its proximal ends are longitudinally opposing. The electrotherapy arrangement further comprises an electrotherapy signal generator circuit electrically coupled with the at least two electrodes and applying electrotherapy signaling to the electrotherapy site via the at least two electrodes. The electrotherapy signaling generates an electric field through the electrotherapy site that is generally uniformly distributed along a longitudinal reference axis located in the electrotherapy site between the anode and cathode of the at least two electrodes.

According to another aspect of the invention, an implantable electrode assembly includes an implantable substrate and three elongate electrodes secured to the substrate. Each electrode has respective proximal and distal opposing ends, and the electrodes are relatively situated such that each electrode is generally uniformly spaced along its length with respect to its adjacent electrode(s). The electrodes are also relatively spaced such that an inner electrode is flanked on two sides by a pair of outer electrodes. A first lead is connected to the inner electrode at the inner electrode's proximal end positioned on one side of the substrate, and second and third leads are connected to the outer electrodes at the respective proximal ends positioned on an opposite side of the substrate. In one embodiment, each of the leads for the outer electrodes are positioned on one side and the lead for the inner electrode is positioned on the opposite side.

In an alternate embodiment, all of the leads are arranged on one side and a portion of the lead to the inner electrode is routed across the substrate within an insulator for the distal end of the lead to connect to the proximal end of the electrode.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

Figure 1A:
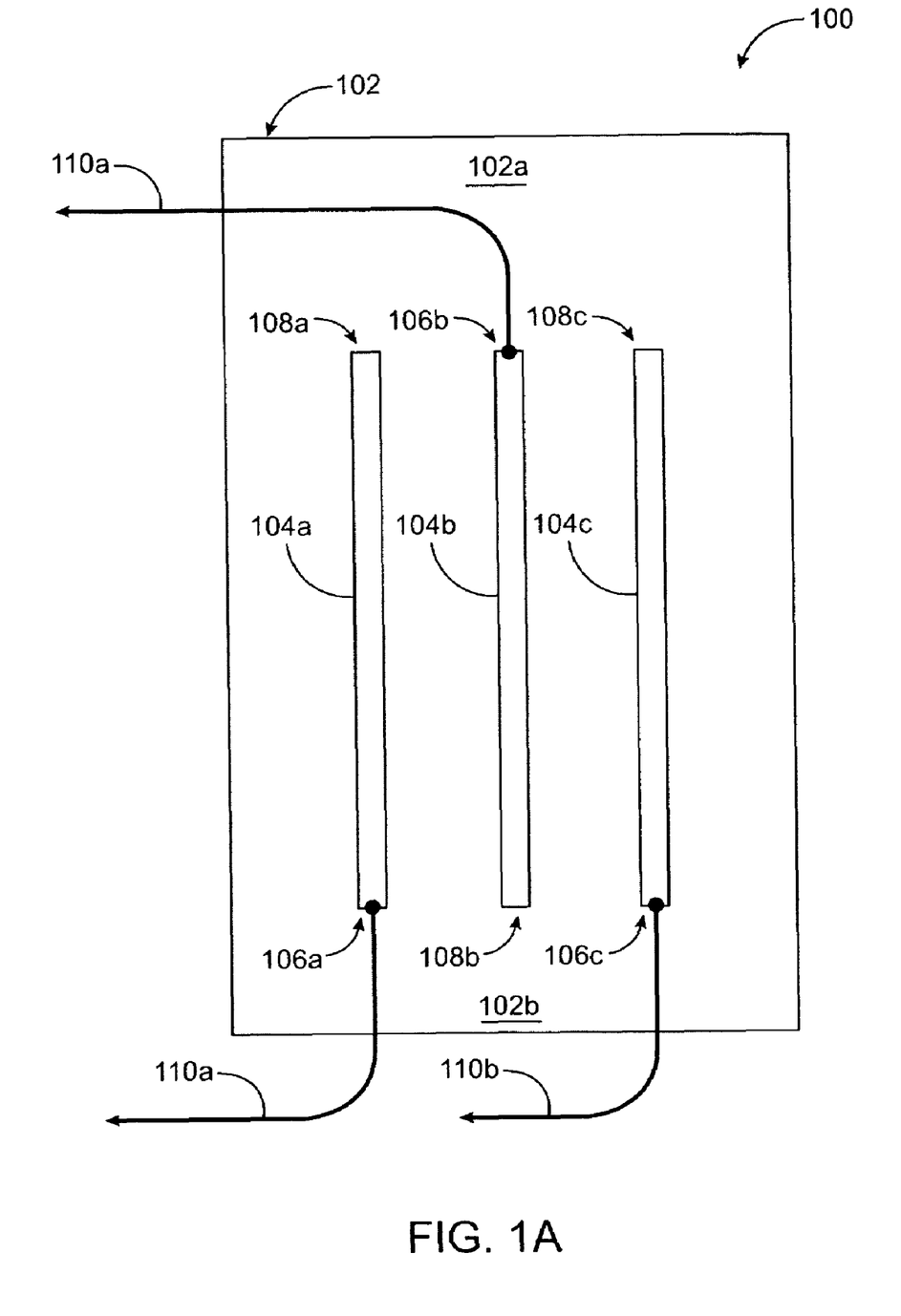
FIG. 1A is a top-view diagram illustrating an electrode assembly according to one embodiment of the present invention.

FIG. 1A is a diagram illustrating an implantable electrode assembly 100 according to one example embodiment of the invention. Electrode assembly 100 can be utilized in a variety of applications including, but not limited to, electrotherapy or stimulation of the patient. Tissue regions that are potential targets of electrotherapy/electrostimulation include the patient's nervous system (including nerve cells and synapses, and sensory receptors such as baroreceptors), muscle tissue, organs, and blood vessels. Electrode assembly 100 includes a base structure or substrate 102 that includes a flexible and electrically insulating material suitable for implantation, such as silicone, optionally reinforced with a flexible material such as polyester fabric. Base structure or substrate 102 can be sized and shaped according to the implantation site for the target tissue region (e.g., targeted blood vessels, muscles, nerves, skin, bone, organs, cells, etc.), and can have flexible and/or elastic properties. Thus, for example, base structure or substrate 102 can have a length suitable to wrap around all (360 degrees) or a portion (i.e., less than 360 degrees) of the circumference of one or more blood vessels.

In one embodiment, electrode assembly 100 includes elongate electrodes 104a-104c for making contact with the target tissue region into which electrotherapy or electrostimulation is to be applied. The electrodes can be un-insulated portions of larger electrical conductors, dedicated un-insulated conductive structures, or a combination thereof. While the elongate electrodes 104a-104c generally extend along a longitudinal axis, it will be recognized that embodiments of the elongate electrodes can include nonlinear geometries such as serpentine, curved or zig-zag, for example, and that in some embodiments not all of an electrode structure need be considered as part of the elongate electrode geometry. In one example embodiment, as illustrated in FIG. 1A, elongate electrodes 104a-104c are each about the same length, and are situated generally parallel to one another such that proximal ends 106a and 106c of outer electrodes 104a and 104c are positioned on the same side 102a of base 102 as distal end 108b of center electrode 104b. On the other side 102b of base 102, distal ends 108a and 108c of outer electrodes 104a and 104c are positioned proximate to proximal end 106b of center electrode 104b on side 102b. For purposes of the present invention it will be understood that proximal is used to reference a region proximate an end of a structure that is electrically closer to the pulse generator and that distal references a region proximate an end of a structure that is further away electrically from the pulse generator as compared to the proximal portion.

In a related type of embodiment, the electrodes are generally co-extensive. Among electrode assemblies of this type, the extent of co-extensiveness can vary according to the geometry of the implantation site. For example, in one example embodiment, the electrodes are co-extensive to within +/−25%. In another embodiment, the electrodes are co-extensive to within +/−5%. While this embodiment features one arrangement of three electrodes 104a-104c in accordance with the present invention, other arrangements and configurations of electrodes 104 as described hereinafter may also be utilized to enhance the uniform distribution of the electric field delivered through the electrodes to the target tissue region.

Electrodes 104a-104c are made from a suitable implantable material, and are preferably adapted to have flexible and/or elastic properties. Electrodes 104a-104c can comprise round wire, rectangular ribbon or foil formed of an electrically conductive and radiopaque material such as platinum. In one embodiment, the base structure 102 substantially encapsulates the conductive material, leaving only exposed electrode 104a-104c portions for electrical connection to the target tissue. For example, each conductive structure can be partially recessed in the base 102 and can have one side exposed along all or a portion of its length for electrical connection to target tissue. The exposed portions constitute electrodes 104a-104c. In another embodiment, the electrodes 104a-104c are made from conductive structures that can be adhesively attached to the base 102 or can be physically connected by straps, moldings or other forms of operably securing them to the base 102. Electrical paths through the target tissue are defined by anode-cathode pairs of the elongate electrodes 104a-104c. For example, in one embodiment, center electrode 104b is a cathode, and outer electrodes 104a and 104c are both anodes, or vice-versa. Thus, electrons of the electrotherapy or electrostimulus signaling will flow through the target region either into, or out of, electrode 104b.

Each electrode 104a-104c is connected at the corresponding proximal end 106a-106c to an electrotherapy/electrostimulus source, such as an implantable pulse generator (not shown) via a corresponding lead 110a-110c. In one example embodiment, leads 110a-110c are each an insulated wire formed with, welded to, or suitably interconnected with each corresponding electrode 104a-104c. Persons skilled in the art will appreciate that leads 110a-110c can be made of any suitable materials or geometries. Furthermore, leads 110a-110c can each include a combination of conductor types. Thus, for example, leads 10a-110c can each include an insulated stranded wire portion, an un-insulated solid wire portion, and/or a coiled wire portion having helical, spiral, or other such coiled geometry.

Figure 1B:
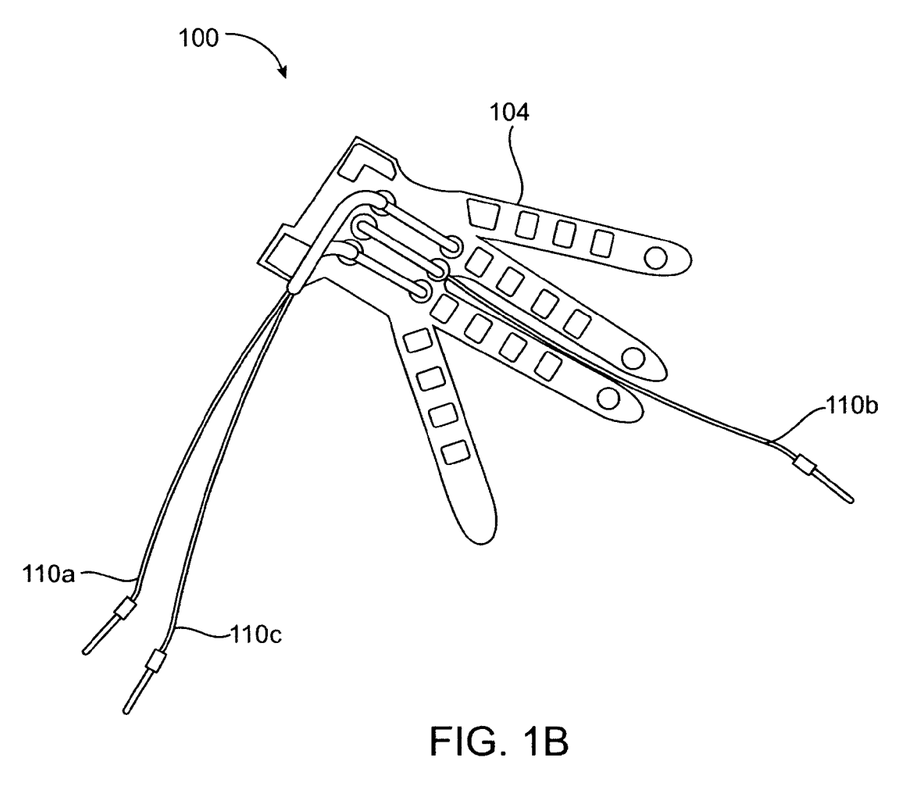
FIG. 1B is a diagram illustrating one physical embodiment of the electrode assembly of FIG. 1A.

FIG. 1B illustrates a physical embodiment of the example electrode assembly 100 of FIG. 1A. The shape of base structure or substrate 102 includes finger-type extensions 112, and reinforced portions 114 for facilitating wrapping and securing the electrode assembly 100 to the implantation site during implantation. Because leads 110a and 110c are connected at opposite electrode ends from lead 110b, leads 110a and 110c naturally extend in a different direction away from the electrodes 104 than the direction of lead 10b. In certain applications, it may be desirable for the leads to extend in the same direction away from the electrodes 104.

Figure 1C:
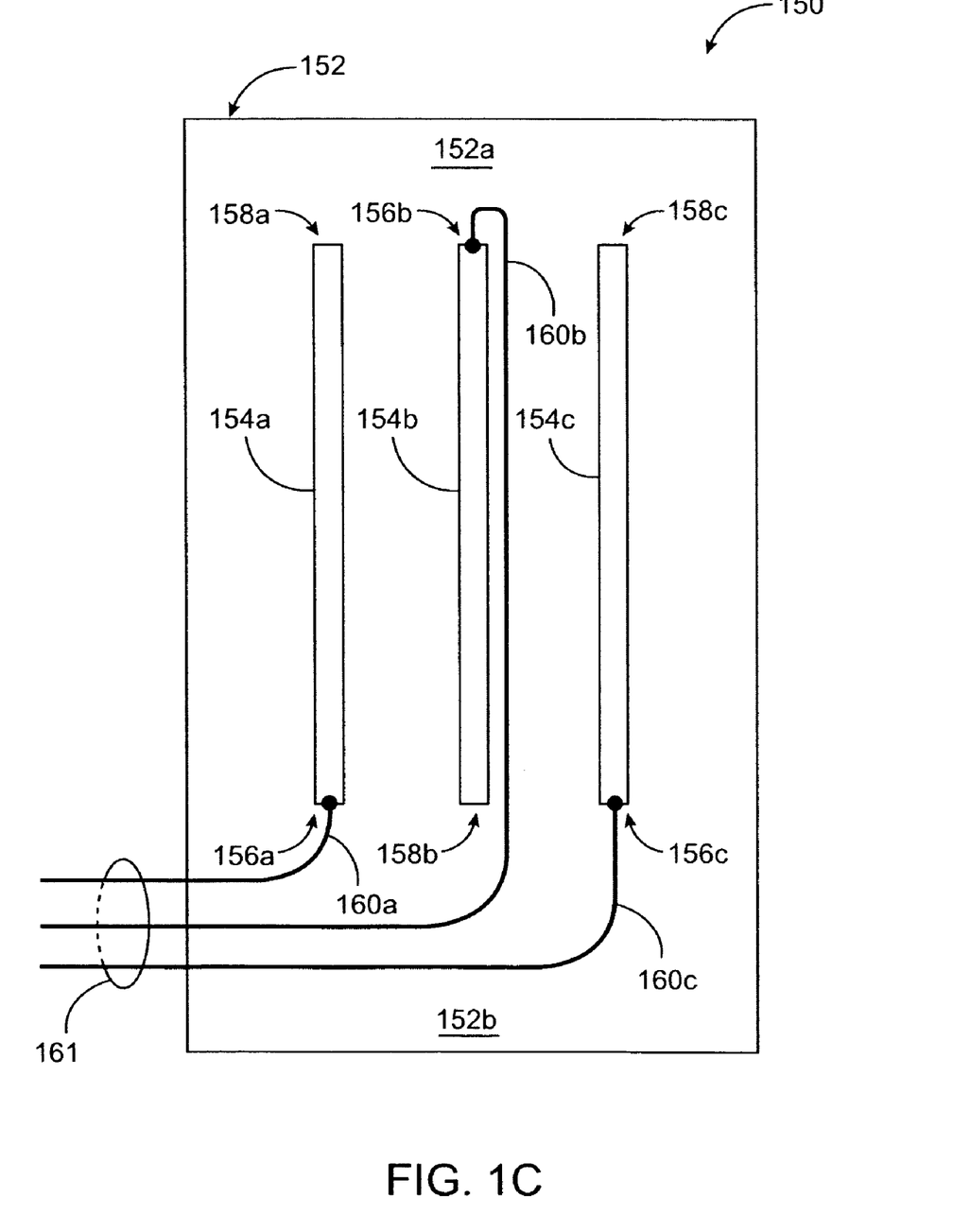
FIG. 1C is a top-view diagram illustrating an electrode assembly having a particular wiring arrangement according to one embodiment of the invention.

FIG. 1C is a diagram illustrating example electrode assembly 150 according to a related embodiment. Electrode assembly 150 includes a flexible and stretchable implantable substrate 152, to which elongate electrodes 154a-154c are secured. Electrodes 154a and 154c are connected respectively to leads 160a and 160c at proximal ends 156a and 156c located on side 152a of substrate 152. Electrode 154b is connected to lead 160b at proximal end 156b located on side 152b of substrate 152. Distal ends 158a and 158c of electrodes 154a and 154c, respectively, are located on side 152b and are not connected to any leads. Distal end 158b of electrode 154b is located on side 152a and is not connected to any lead. Lead 160b extends along the length of electrode 154b towards distal end 156b, and further extends in the same direction as leads 160a and 160c, as illustrated in FIG. 1C. The leads 160a-160c are optionally bundled and secured together by wire tie 161.

Figure 1D:
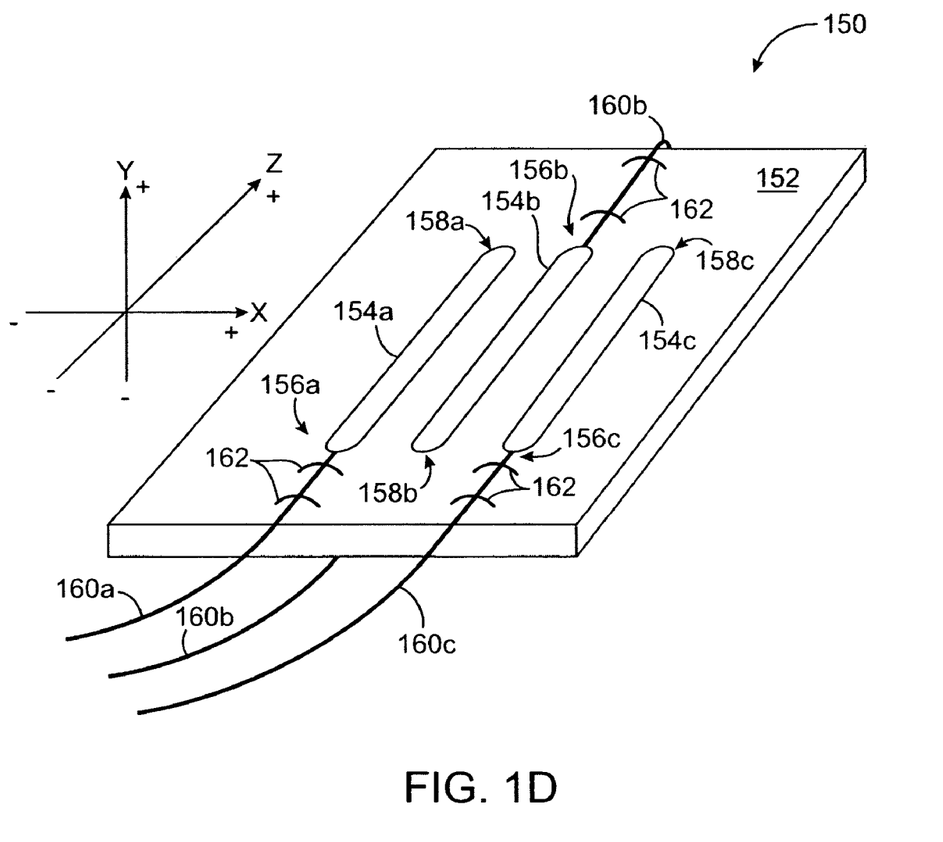
FIG. 1D is a perspective view diagram illustrating an example physical layout of the electrode assembly of FIG. 1C in which the lead connecting one of the electrodes to the signal generator runs along the bottom surface of the substrate.

FIG. 1D illustrates a physical embodiment of example electrode assembly 150. Electrodes 154a-154c are secured to substrate 152, and are oriented along the reference z-axis. Insulated leads 160a-160c are attached to their respective electrodes as shown. Leads 160a and 160b are connected to respective electrodes 154a and 154c at respective proximal ends 156a and 156c. Lead 160b is connected to electrode 154b at proximal end 156b. Leads 160a and 160c extend in the −z direction away from their corresponding electrodes 154a and 154c, and proceed in the −x direction. Lead 160b extends away from electrode 154b in the +z direction, then loops around substrate 152, and further proceeds in the −z along the underside of substrate 152. Leads 160a-160c are secured to substrate at various points by anchors 162 as shown. Lead 162b is also secured at points along the underside surface of substrate 152 by anchors 162 (not shown).

Figure 1E:
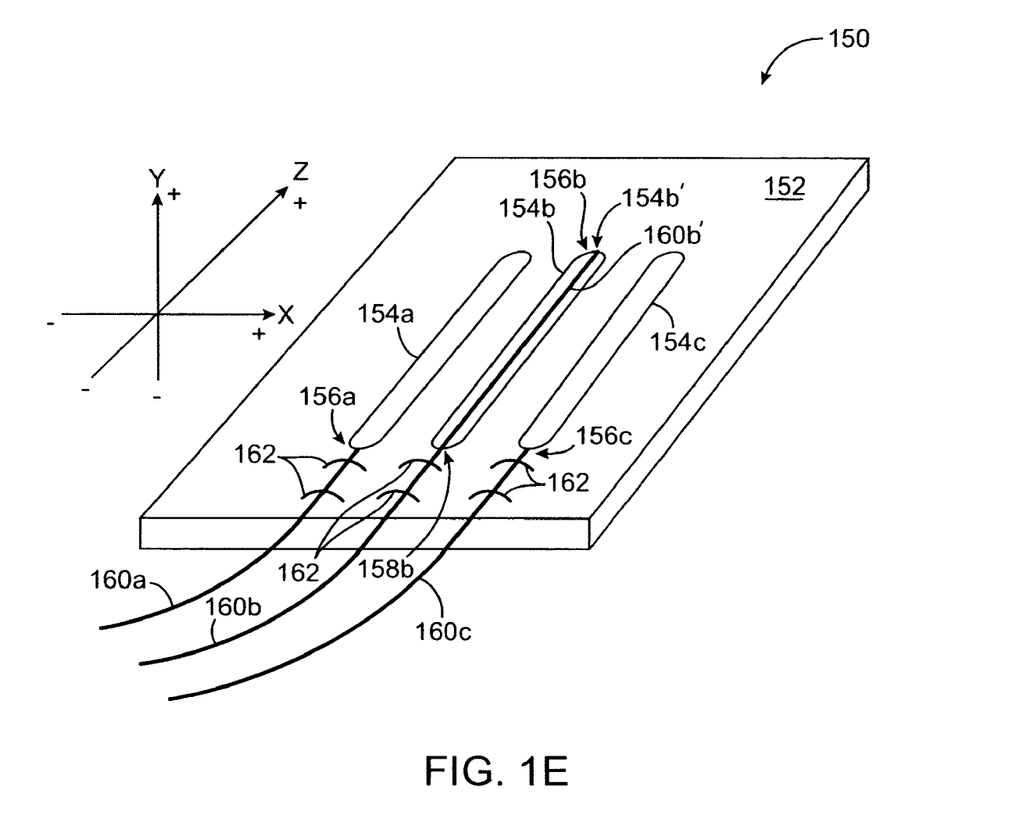
FIG. 1E is a perspective view diagram illustrating another example physical layout of the electrode assembly of FIG. 1C in which at least one of the electrodes is formed around a portion of the lead connected with the electrode.

FIG. 1E illustrates another example physical layout of the electrode assembly 150. In this embodiment, electrode 154b is formed from an elongate structure having a hollow core 154b'. Lead 160b enters core 154b' at an opening at distal end 158b and passes through core 154b' of the elongate structure to proximal end 156b, at which point lead 160b connects with electrode 154b. In one example embodiment, lead 160b includes a portion 160b' that is specially adapted to be situated within core 154b'. Optionally, electrodes 154a and 154c are adapted to be pliably compatible with the structure of electrode 154b having a portion of lead 160b in its core 154b'.

Figure 1F:
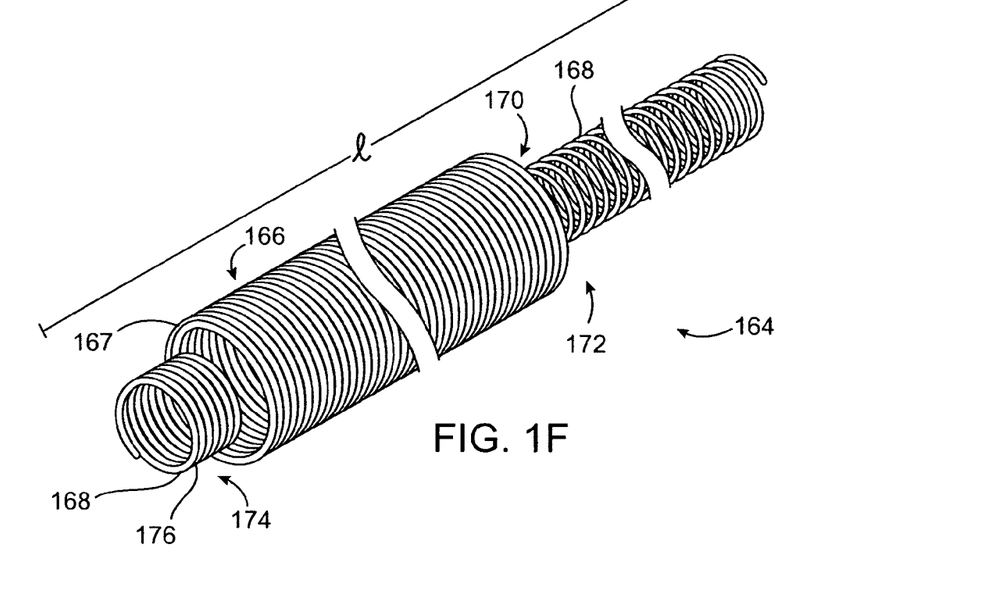
FIG. 1F is a perspective view diagram illustrating one example physical embodiment of a coiled outer electrode structure formed around an inner coiled lead portion that is connected to the electrode at a proximal end.
Figures 1G, 1H:
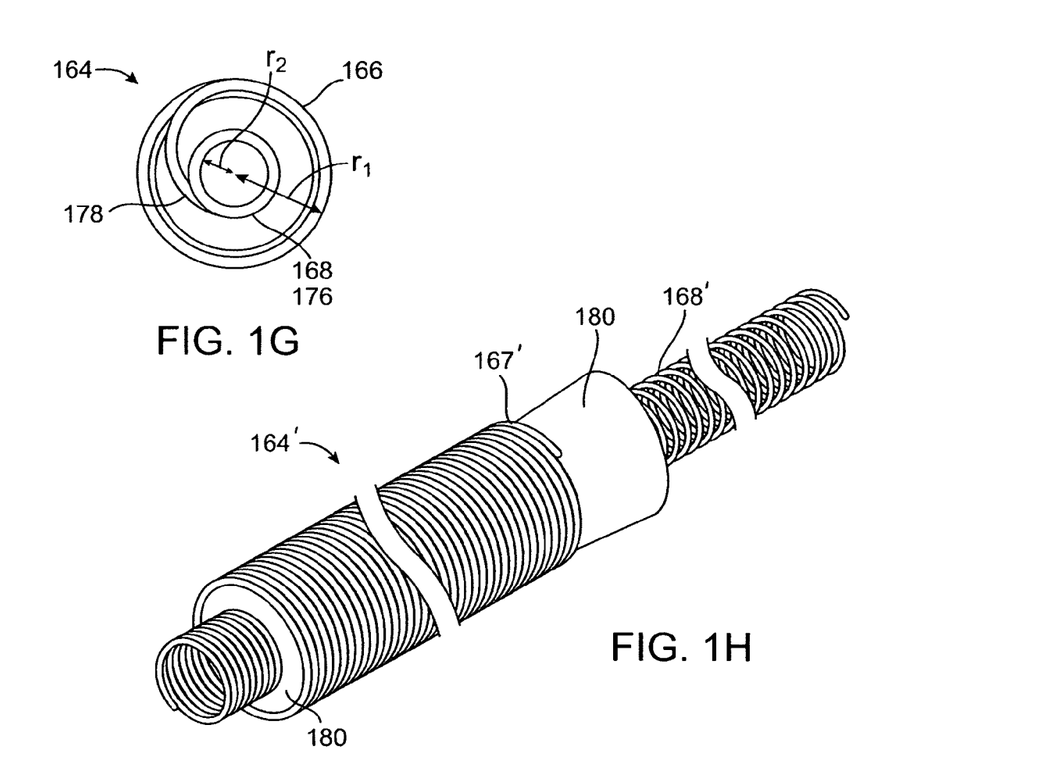
FIG. 1G is an end-view diagram of the electrode structure of FIG. 1F.
FIG. 1H is a perspective view diagram illustrating another example physical embodiment of a coiled outer electrode structure formed around an inner coiled lead portion that is connected to the electrode at a proximal end, in which an insulator is positioned between the outer electrode and inner conductor portion.

FIGS. 1F-1H illustrate various example electrode structures that each include an elongate electrode portion in the shape of a coil formed around a portion of a lead that is connected to the electrode portion at the proximal end. Structure 164 of FIG. 1F is an elongate structure having a length l. Structure 164 has an outer coiled portion 166 made of non-insulated wire and generally helical in its geometry. At least a portion of structure 164 can operate as an electrode when in contact with target tissue. Structure 164 further includes a generally helical inner coiled portion 168 passing through the core 170 defined by the wire of outer coiled portion 166. Inner coiled portion 168 is thus circumscribed along at least a portion of its length by outer coil portion 166. One type of wire material that can be suitable for certain implantable applications is 80/20 Pt/Ir. However, persons skilled in the art will recognize that other suitable materials may be used. Inner coiled portion 168 enters core 170 at distal end 172, and helically extends through core 170 towards proximal end 174, at which point inner coiled portion 168 makes contact with outer coiled portion 166.

In one example embodiment, near proximal end 174, one or more windings of outer coiled portion 166 have a progressively reducing radius as they approach proximal end 174 such that, at proximal end 174, windings of outer coiled portion 166 have approximately the same radius as the windings of inner coiled portion 168. This embodiment is illustrated in FIG. 1F. Outer coiled portion 166 includes windings 167 having a relatively larger radius, and windings 176 having a relatively smaller radius. Reduced radius windings 176 are situated in a bifilar arrangement at proximal end 174 with the windings of inner coiled portion 168. FIG. 1G is an end view of structure 164 illustrating this embodiment. Outer coiled portion 166 includes windings 167 having larger radius $r_1$, and windings 176 near the proximal end 174 having smaller radius $r_2$. Winding 178 of outer coiled portion 166 integrally bridges the larger radius windings 167 with the smaller radius windings 176. In one embodiment, at proximal end 174, the wire forming outer coiled portion 166 is welded to the wire forming inner coiled portion 168. Persons skilled in the art will appreciate that other suitable mechanisms of creating an electrical contact between these wires, including, but not limited to, soldering, crimping, twisting, or conductively adhesively bonding, may be utilized.

In one embodiment, inner coiled portion 168 is positioned relative to larger outer coiled portion 166's windings 167 such that, in operation, the inner coiled portion 168 and outer coiled portion 166 do not make contact at any point other than at the proximal end 174. In one embodiment, inner coiled portion 168 is formed from insulated wire. In another embodiment, inner coiled portion 168 is formed from un-insulated wire, but inner surfaces of windings 167 are insulated. In another embodiment, the radius of the inner coiled portion's windings $R_2$ is sized relatively to the outer coiled portion's windings 167 having larger radius $r_1$ such that undesired contact points are not created when the structure 164 is elastically flexed to a maximum limit.

In another type of embodiment, as illustrated in FIG. 1H, structure 164' includes an insulating material 180 that is coaxially situated between inner coiled portion 168' and large-radius coils 167' of outer coiled portion 166'. According to one example of this type of embodiment, as illustrated in the side view diagram of FIG. 1I, the radii of inner coiled portion 168' and of outer coiled portion 167' remain generally constant over the length of the structure (disregarding the change in radius of the outer portion near the proximal end). Insulator 180 has a generally cylindrical outer wall that is adjacent to outer coiled portion coils 167', and a generally cylindrical inner wall adjacent to inner coiled portion 168'.

Figure 1I:
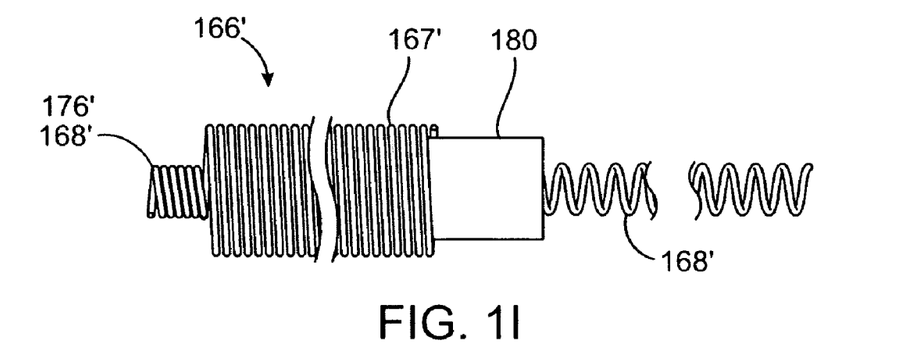
FIG. 1I is a side-view diagram illustrating an example coiled electrode structure of the type illustrated in FIG. 1H, in which the outer and inner coils are generally helical in geometry and in which the insulator is generally cylindrical in geometry.
Figure 1J:
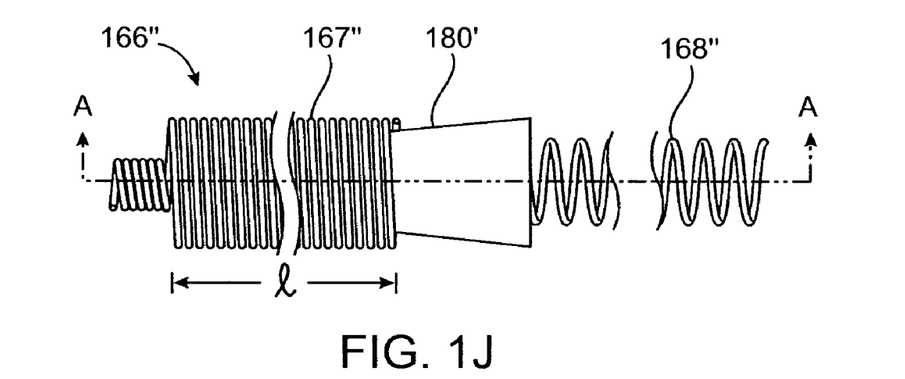
FIG. 1J is a side view diagram illustrating an example coiled electrode structure of the type illustrated in FIG. 1H, in which the inner coil has a spiral geometry wherein coil radius decreases towards the proximal end, and in which the insulator has a geometry wherein the walls have a profile of decreasing radius that corresponds to the decreasing radius profile of the inner coil.
Figure 1K:
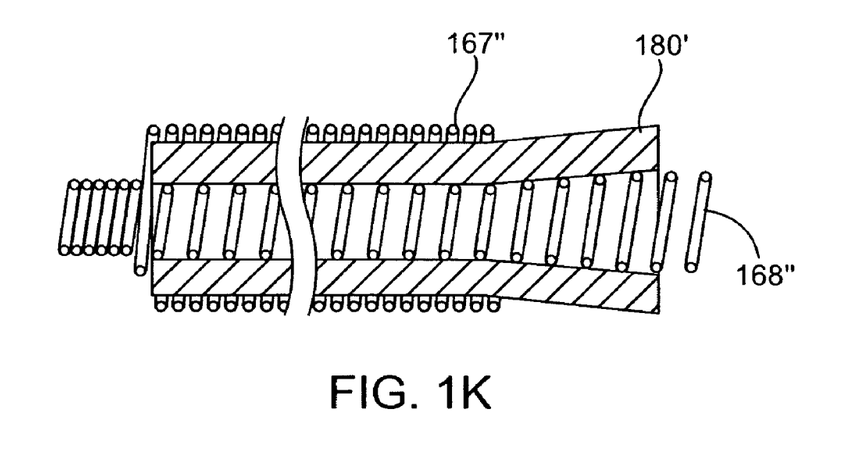
FIG. 1K is a cross-sectional view diagram of the electrode structure of FIG. 1J.

FIGS. 1J and 1K illustrate an example of a variation of the embodiment of FIG. 1I. FIGS. 1J and 1K are, respectively, side view diagrams of a structure in which large-radius coils 167" of outer coiled portion 166" have a constant radius over length l, but inner portion 168" has a spiral geometry in which the coil radius decreases towards the proximal end. The radii of outer and inner walls of insulator 180' also have a profile of decreasing radius that corresponds to the decreasing radius profile of inner coils 168". According to one aspect of this embodiment, the geometry of the structure of FIGS. 1J and 1K provides a benefit of securing in place the insulator 180' by preventing it from sliding towards either end of the structure.

In the configuration of electrodes 104a-104c (FIGS. 1A and 1B) and 154a-154c (FIGS. 1C, 1D, and 1E), having the electrode/lead connections at opposite ends for electrodes of opposite polarity provides improved electric field uniformity and improved corrosion resistance as compared against equivalent configurations having the connections at the same end. FIGS. 2-5, described in detail below, illustrate these principles.

Figure 2:
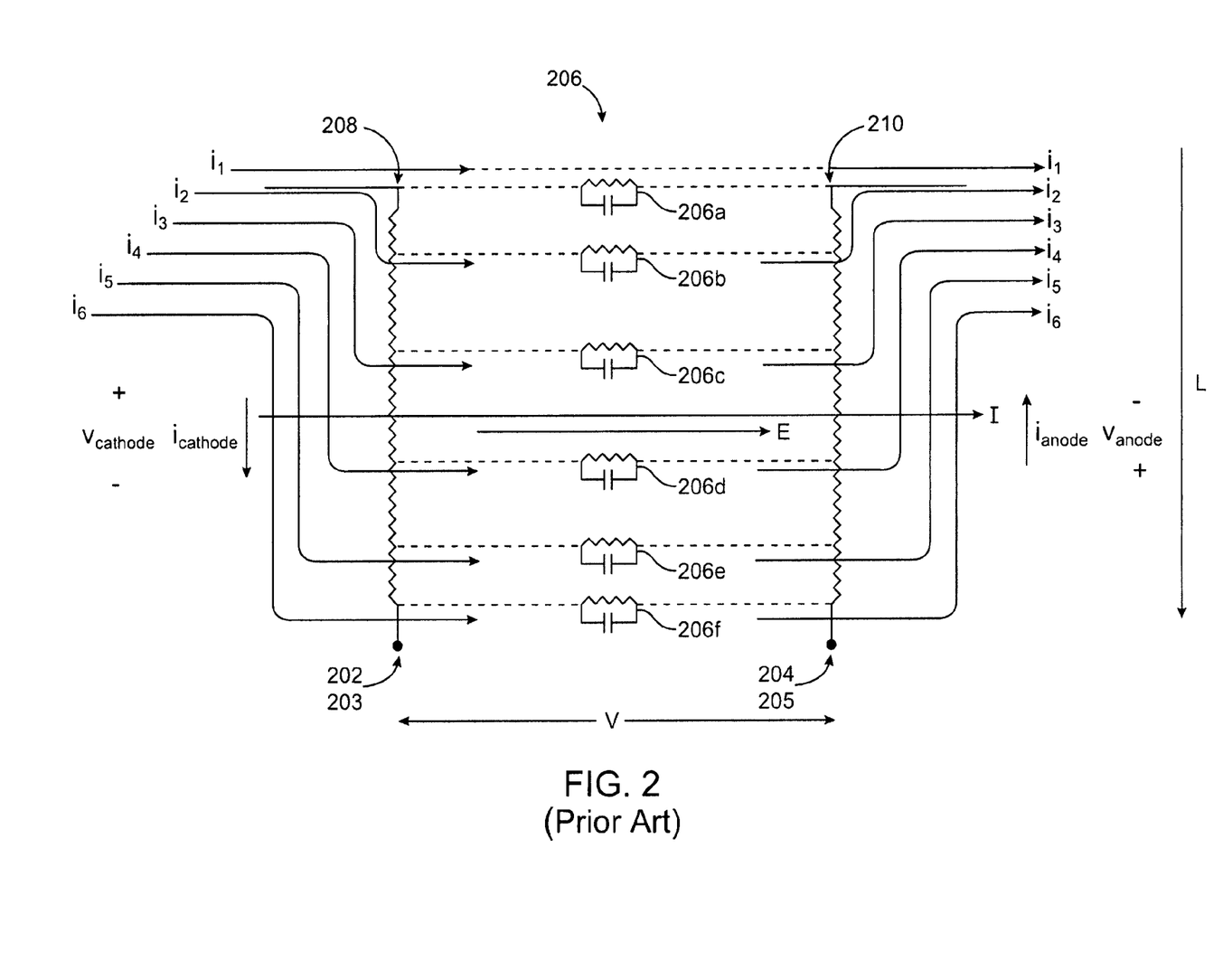
FIG. 2 is a schematic diagram illustrating functional aspects of electrode assemblies known in the art.

FIG. 2 is a diagram illustrating an electrical circuit model of a state-of-the-art implanted electrode assembly. Distributed resistance 202 represents one or more cathodes 203 connected to the electrotherapy/electrostimulus signal generator. Likewise, distributed resistance 204 represents one or more anodes 205 connected to the opposite pole of the electrotherapy/electrostimulus generator. Distributed resistances 202 and 204 are each distributed over the length L and quantity of their corresponding electrode(s), and are not necessarily equal in magnitude. Target tissue impedance 206 represents the electrical properties of the target tissue interconnecting the electrodes. Target tissue impedance 206 is modeled as a set of parallel resistor-capacitor pairs 206a-206f distributed over the aggregate volume V that separates the cathode(s) from the anode(s). The resistance of each electrode's distributed resistance 202 and 204 is generally evenly distributed over length L. With increasing length L, the resistance component of impedance 206 decreases, whereas the capacitance component increases.

Cathode 203 is connected to the signal generator at top end 208; anode 205 is connected to the opposite pole of the signal generator at top end 210. When the electrotherapy/electrostimulus signal is applied across electrodes 203 and 205, an aggregate current I generally passes through the resistive component of the target tissue having impedance 206. Also, an aggregate electric field E generally exists across the electrodes 203 and 205 due to the capacitive component of impedance 206. However, due to the distributed resistances of the electrodes 203 and 205, as well as the distributed target tissue impedance 206, the current I and electric field E are also distributed over the length L and volume V. The distribution of current I and electric field E depends on the distribution of tissue impedance 206, and on the charge distribution over the length L of each electrode 203 and 205.

Within each of the distributed electrode resistances 202 and 204, there exist a cathode current $i_{cathode}$ and $i_{anode}$, and corresponding voltage drops $v_{cathode}$ and $v_{anode}$. These currents and voltages occur within each elongate electrode because the electrode resistances 202 and 204 create voltage and current divisions with respect to signal paths through the target tissue. Because the signal generator connections are located at the top ends 208 and 210 of electrodes 203 and 205, respectively, the cathode and anode currents and voltages have opposite directions and polarities, as illustrated in FIG. 2.

Figure 3:
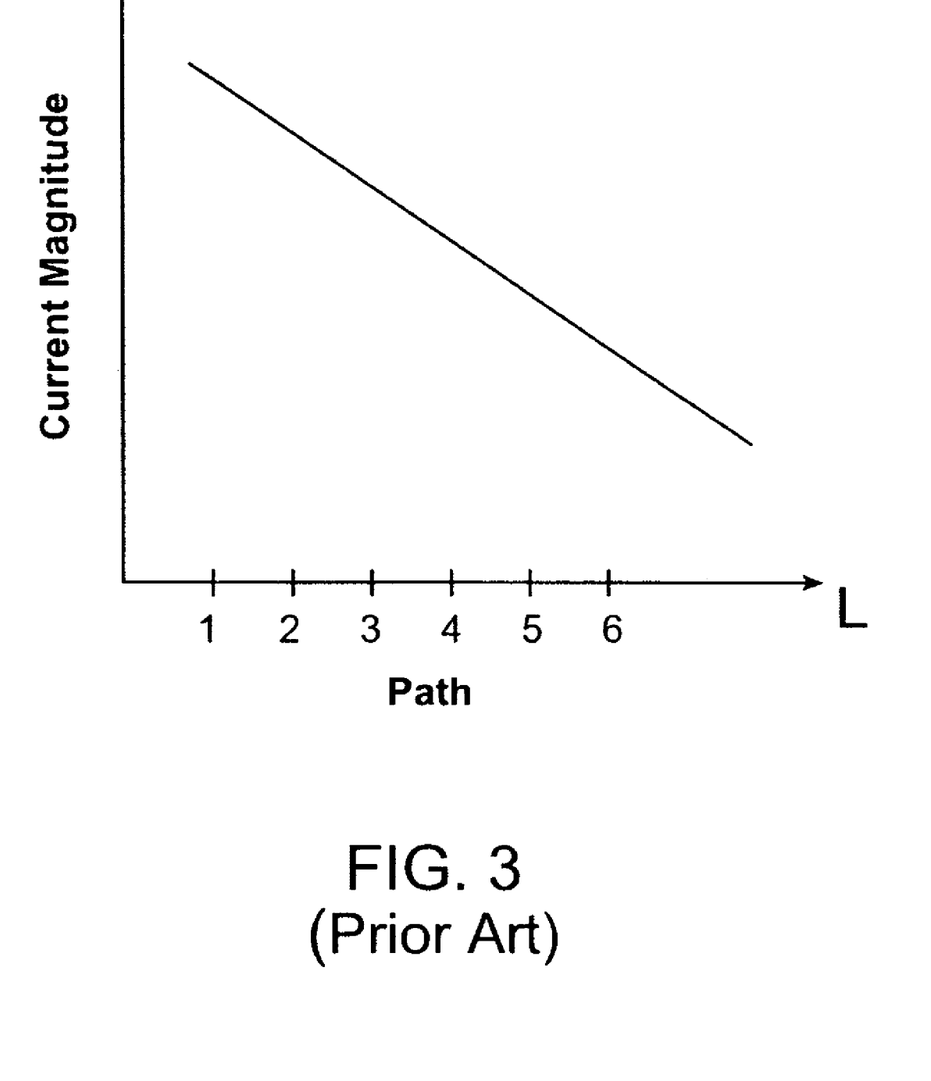
FIG. 3 is a chart illustrating the current distribution through target tissue during operation of the electrodes represented in the schematic of FIG. 2.

As a result, the distributed current I and electric field E through the target tissue region are not evenly distributed. By way of example, discrete current components $i_1$-$i_6$ located successively at greater distances from the top ends 208 and 210 are successively lower in amplitude such that $i_1$ has the greatest amplitude while $i_6$ has the lowest amplitude. FIG. 3 illustrates an example current distribution through volume V over length L. The axis labeled L corresponds to the L dimension of FIG. 2, and the paths 1-6 correspond to the paths taken by example current components $i_1$-$i_6$.

Figure 4:
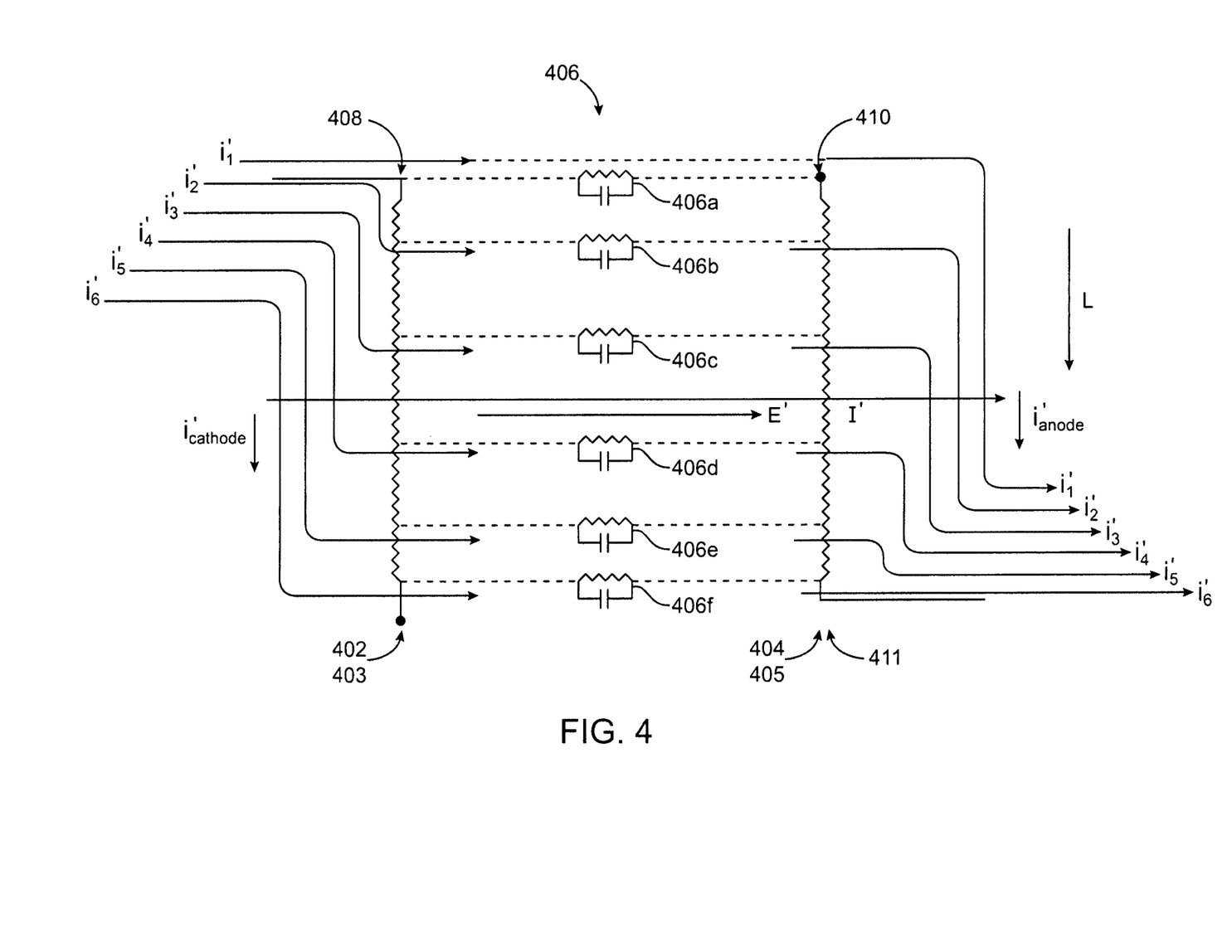
FIG. 4 is a schematic diagram illustrating functional aspects of an electrode assembly according to one embodiment of the present invention.

FIG. 4 illustrates an electrical diagram of an example implanted electrotherapy/electrostimulation electrode assembly according to one embodiment of the present invention. Distributed resistances 402 and 404 represent aggregate elongate electrodes 403 and 405, respectively. Electrodes 403 and 405, and the target tissue having impedance 406 are all correspondingly similar to their respective analogues described above with reference to FIG. 2. The only difference in the arrangement between the example of FIG. 2 and the example of FIG. 4 is the connection of the signal generator to the cathode and anode. Cathode 403 is connected to the signal generator at top end 408; whereas anode 405 is connected at bottom end 411. As a result of this reversal, the bottom end 411 is more negatively charged than the top end 410 of the anode 405. This causes the charge density of the electrodes 403 and 405 to be evenly distributed along the length L, which results in an even distribution of aggregate current I' and aggregate electric field E'. Thus, example discrete current components $i_1'$-$i_6'$ each pass through an equivalent impedance. For instance, current component $i_2'$ passes through a smaller portion of cathode impedance 402, through target tissue impedance component 406b, and through a larger portion of anode impedance 404; whereas current component $i_5'$ passes through a larger portion of cathode impedance 402, an equivalent target tissue impedance component 406e, and through a smaller portion of anode impedance 404.

Figure 5:
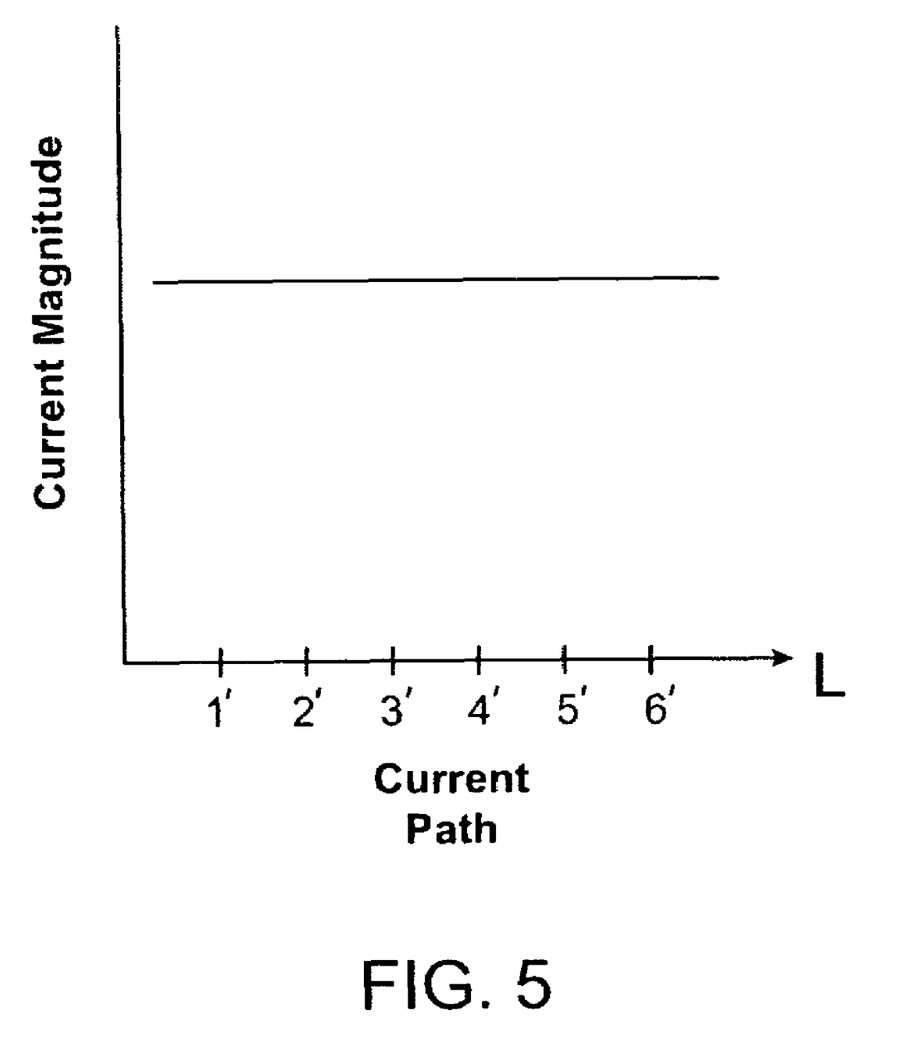
FIG. 5 is a chart illustrating the current distribution through target tissue during operation of the electrodes represented in the schematic of FIG. 4.

Another result of the electrode arrangement of FIG. 4 is that the cathode current $i_{cathode}'$ is directed along the same direction as the anode current $i_{anode}'$. FIG. 5 illustrates the uniform distribution of aggregate current I' over length L for the example electrode assembly configuration of this embodiment.

By distributing the charge density evenly over each of the electrodes 403 and 405, any faradaic processes are also distributed over the surfaces of the electrodes. This effect results in an increased corrosion threshold because electrode corrosion is based on the charge density. Another effect is an increase in capacitance seen by the electrotherapy or electrostimulation signaling. Because the charge density is evenly distributed along length L, the signaling sees a greater overall target tissue capacitance. With an increased overall capacitance created by the charge balancing, more of the activation current is used to charge the electrode double layer and less is available for faradaic processes. The charging of the electrode double layer results in an induced current in the target tissue resulting in the desired stimulation or therapeutic effect.

Figure 6:
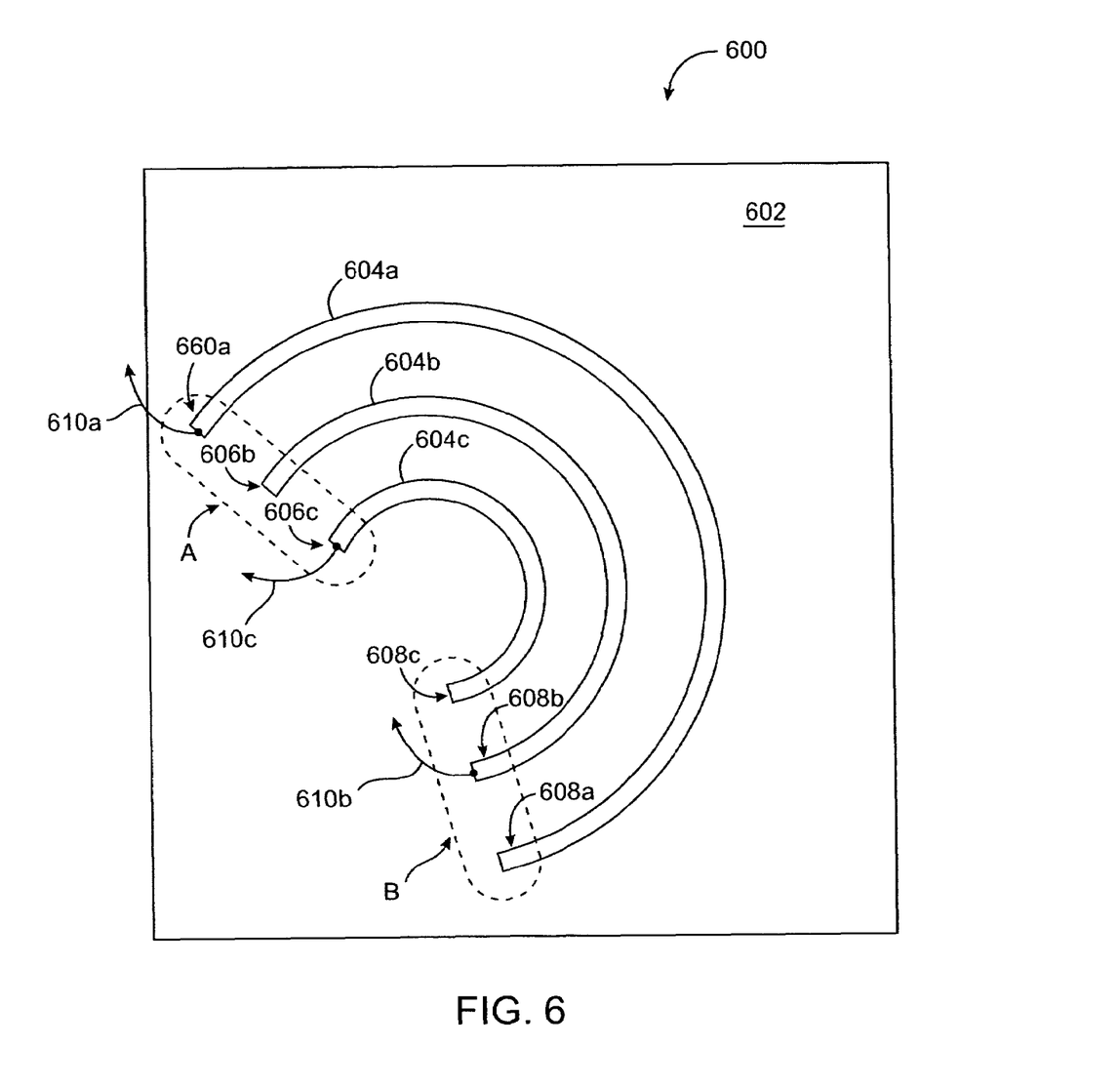
FIG. 6 is a diagram illustrating an electrode assembly according to one embodiment of the present invention in which the electrodes are non-linear.

The present invention contemplates a variety of electrode forms or shapes, not necessarily limited to straight linear segments. FIG. 6 is a diagram illustrating an example electrode assembly 600 according to another embodiment of the present invention. Electrode assembly 600 includes a flexible substrate 602 to which arcing elongate electrodes 604a-604c are secured. Arcing elongate electrodes 604a-604c each have a first end in a first region A and a second end in a second region B such that the electrodes 604a-604c arcuately extend between regions A and B. Electrode 604a has a lead 610a electrically connected to its first end 606a. Electrode 604b has a lead 610b electrically connected to its second end 608b. Electrode 604c has a lead 610c electrically connected to its first end 606c. For electrodes 604a and 604c, respective second ends 608a and 608c have no leads connected thereto. Conversely, for electrode 604b, first end 606b is free of any lead connection. When implanted in a patient, electrodes 604a-604c are electrically interconnected by the target tissue. In operation, the charge distribution in each of the electrodes is approximately uniform, resulting in electric fields and currents approximately uniformly distributed through the interconnecting target tissue.

The invention may be embodied in other specific forms without departing from the essential attributes thereof; therefore, the illustrated embodiments should be considered in all respects as illustrative and not restrictive.

What is claimed is:

1. An implantable electrode assembly comprising:
   an implantable substrate;
   three elongate electrodes secured to the substrate, each electrode having respective proximal and distal opposing ends, wherein the electrodes are relatively situated such that each electrode is generally uniformly spaced along its length with respect to at least one adjacent electrode, and an inner electrode is flanked on two sides by a pair of outer electrodes;
   wherein a first lead is connected to the inner electrode at the inner electrode's proximal end positioned on one side of the substrate; and
   wherein a second lead and a third lead are connected to the outer electrodes at the respective proximal ends positioned on an opposite side of the substrate.

2. The electrode assembly of claim 1, wherein at least a portion of the implantable substrate is flexible.

3. The electrode assembly of claim 1, wherein the three elongate electrodes are general parallel with one another.

4. The electrode assembly of claim 1, wherein each outer electrode is equidistantly spaced with the inner electrode.

5. The electrode assembly of claim 1, wherein distal ends of the outer electrodes are generally collinear with the proximal end of the inner electrode.

6. The electrode assembly of claim 1, wherein the proximal ends of the outer electrodes are generally collinear with a distal end of the inner electrode.

7. The electrode assembly of claim 1, wherein the electrodes are non-linearly disposed along their lengths.

8. The electrode assembly of claim 1, wherein the distal ends of the outer electrodes are-generally collinear with a proximal end of the inner electrode.

9. The electrode assembly of claim 1, wherein at least one of the first, second and third leads is insulated.

10. The electrode assembly of claim 1, wherein the first lead is situated such that the first lead generally extends from a proximal end of the inner electrode towards a distal send of the inner electrode.

11. The electrode assembly of claim 10, wherein the first lead is circumscribed along at least a part of its length by at least a part, of the inner electrode.

12. The electrode assembly of claim 1, wherein the second lead and the third lead are situated such that each lead extends from a proximal end of a corresponding one of the pair of outer electrodes towards a distal end of the corresponding one of the pair of outer electrodes.

13. The electrode assembly of claim 12, wherein the second lead and the third lead are circumscribed along at least a part of their length by at least a part of the corresponding one of the pair of outer electrodes.

* * * * *